(12) United States Patent
Voskoboynikov et al.

(10) Patent No.: US 8,426,613 B2
(45) Date of Patent: Apr. 23, 2013

(54) SYNTHESIS OF SUBSTITUTED TETRAHYDROINDENYL COMPLEXES

(75) Inventors: Alexander Z. Voskoboynikov, Moscow (RU); Vyatcheslav V. Izmer, Moscow (RU); Dmitry S. Kononovich, Moscow (RU); Abbas Razavi, Mons (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 0 days.

(21) Appl. No.: 13/140,455

(22) PCT Filed: Dec. 15, 2009

(86) PCT No.: PCT/EP2009/067161
§ 371 (c)(1),
(2), (4) Date: Aug. 30, 2011

(87) PCT Pub. No.: WO2010/076188
PCT Pub. Date: Jul. 8, 2010

(65) Prior Publication Data
US 2011/0306741 A1      Dec. 15, 2011

(30) Foreign Application Priority Data

Dec. 30, 2008   (WO) ............... PCT/RU2008/000814

(51) Int. Cl.
| | | |
|---|---|---|
| *C07C 13/64* | (2006.01) |
| *C07C 13/32* | (2006.01) |
| *C07D 333/00* | (2006.01) |
| *C07D 495/00* | (2006.01) |
| *C07F 17/00* | (2006.01) |
| *C08F 4/6592* | (2006.01) |

(52) U.S. Cl.
USPC ................ 549/3; 585/442; 585/446; 556/53; 549/4; 526/160; 526/943

(58) Field of Classification Search ................ 549/3, 4; 556/53; 585/442, 446; 526/160, 943
See application file for complete search history.

(56) References Cited

U.S. PATENT DOCUMENTS 5,883,275 A    3/1999   Bingel et al.
5,990,331 A   11/1999   Winter et al.

*Primary Examiner* — Caixia Lu

(57) ABSTRACT

This invention relates to the synthesis of substituted tetrahydroindenyls and the use of the synthesized complexes in the homo- and co-polymerization of ethylene and alpha-olefins.

6 Claims, 5 Drawing Sheets

SYNTHESIS OF SUBSTITUTED TETRAHYDROINDENYL COMPLEXES

CROSS-REFERENCE TO RELATED APPLICATIONS

This application claims the benefit of PCT/EP2009/067161, filed Dec. 15, 2009, which claims priority from PCT/RU20081000814, filed Dec. 30, 2008.

This invention relates to the synthesis of substituted tetrahydroindenyls.

A C2-symmetric metallocene catalyst component can appear in two stereo-isomeric forms: a racemic form and a meso form. A stereospecific catalyst is used to prepare stereoregular polyolefins. It is generally known that the racemic form induces a reproducible orientation of incoming monomers when the catalyst component is used in an olefin polymerisation reaction. This is desirable for producing an isotactic polyolefin.

Attempts have been made either to avoid the production of the meso isomer or to separate the desirable racemic isomer from the meso isomer, but the separation step is costly and it has been observed that after purification the mesa isomer is reintroduced in the system under the effect of light or heat. Hydrogenation of the catalyst component avoids the formation of the meso isomer and/or its "re-formation" under the effect of light or heat. As such, a hydrogenated metallocene catalyst component is known to be useful in olefin polymerisation.

In the specific context of bridged bis-indenyl-based metallocenes, it is known in the art that these give rise to the formation of two isomeric metallocenes (racemic and meso) with different catalytic properties. The non-stereo specific meso component contributes to the formation of an undesirable low molecular weight atactic polymer fraction whereas the racemic component produces a highly stereoregular polymer fraction. In addition, starting from pure racemic ingredients, heat and light induce the transformation of part of the racemic precatalyst into the meso isomer, thereby leading to the formation of lower molecular weight "solubles" after activation and during the polymerisation. This is particularly detrimental in the production of ethylene/propylene copolymers.

It has been observed that hydrogenation of the indenyl rings reduces the production of the meso isomer during the final steps of the metallocene synthesis, but so far hydrogenation has been carried out only on the final catalyst and has been successful for unsubstituted bis-indenyl components and with somewhat success on mono-substituted bis-indenyl components.

J. Organomet. Chem. (1982), 232, 233-247 describes the synthesis of ethylene-bis(4,5,6,7-tetrahydro-1-indenyl)-titanium dichloride. This is made by hydrogenation of ethylene-bis(indenyl)titanium dichloride using either a palladium-on-charcoal hydrogenation catalyst or a $PtO_2$ hydrogenation catalyst. This hydrogenation reaction is said, in principle to give the chiral compound in sufficiently pure form. However, in practice, chromatographic separation is needed in order to eliminate the achiral meso-isomer, which represent a major portion of the product.

EP-A-344887 is concerned with a chiral silicon-bridged metallocene catalyst that polymerises α-olefins with high isotacticity, with a minimum number of inversions and at high rates of catalyst activity. In Example 1, the compound 1,1'-dimethylsilanylene bridged bis(indenyl) zirconium dichloride was prepared. Further, the tetrahydroindenyl derivative of this compound was prepared by adding methylene chloride and platinum black or platinum (IV) oxide. Following hydrogenation, the insoluble racemic isomer was filtered off and crystallised. Similarly in Example 7, tetramethyldisiloxane bridged bis(tetrahydroindenyl) zirconium dichloride was prepared.

Summarising the state of the art as outlined above, U.S. Pat. No. 5,883,275 acknowledges that the synthesis of hydrogenated or partially hydrogenated metallocenes generally starts from the corresponding metallocenes having aromatic ligands. It further is stated that the known synthetic procedures for hydrogenating the aromatic ligand skeleton of metallocenes in principle all follow the same route. The metallocene is dissolved or suspended in dichloromethane and hydrogenated in the presence of platinum back or platinum dioxide under a high pressure of hydrogen. However, U.S. Pat. No. 5,883,275 alleges some disadvantages of these known procedures. It however discloses an alternative method for synthesising hydrogenated metallocene. As in previously known methods, their procedure also starts from the corresponding metallocene having aromatic ligands. However, a new method for hydrogenation is disclosed wherein the metallocene to be treated with hydrogen in the presence of a hydrogenation catalyst is in a non-halogenated solvent. This non-halogenated solvent is essential for making it possible to employ very active hydrogenation catalysts, to carry out the hydrogenation reaction at relatively low hydrogen pressure and to work at temperatures above 0° C.

J. Organomet. Chem., 604 (2000), 12-19, also reports the hydrogenation of bis(indenyl) zirconium dichloride into the corresponding bis(tetrahydroindenyl) zirconium dichloride. It is however further acknowledged that the ability to hydrogenate the six-membered ring in indenyl metal complexes is not general. This document reports a different approach for synthesising bis(tetrahydroindenyl) lanthanum chlorides directly from "pre-reduced" bis(tetrahydroindenyl) ligands. The synthesis of 2-methyl-4,5,6,7-tetrahydroindenyl lithium is shown in scheme 1 of this document. The synthesis of silyl-bridged bis(tetrahydroindene) is shown in Scheme 2.

In view of the above, it will be understood that there is a need for further, and preferably improved, methods for making a hydrogenated metallocene catalyst component, which catalyst component preferably polymerises α-olefins to high isotacticity.

It is an aim of the present invention to provide a method for preparing bridged substituted bis-tetrahydroindenyl catalyst components.

Accordingly, the present invention discloses a method for preparing substituted bis-tetrahydroindenyl ligands that comprises the steps of:

a) preparing a complex of general formula I or formula I'

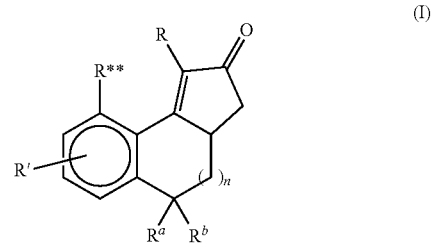

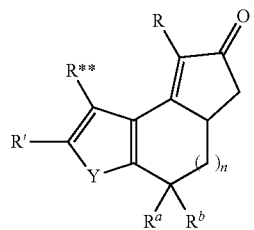
(I')

b) reacting complex I or I' with R"Li, followed by acidification with diluted acid, in order to prepare respectively complex II or complex II'

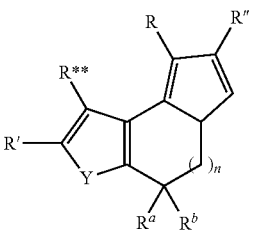
(I)

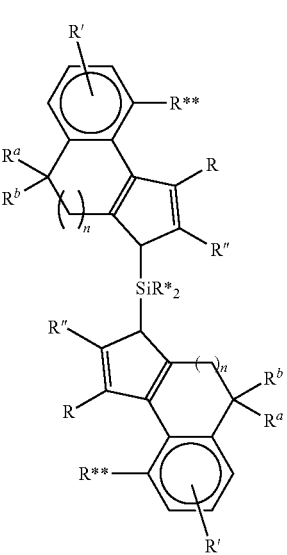
(II')

c) optionally reacting complex II or complex II' with R*$_2$SiX$_2$ in the presence of $^n$BuLi in order to prepare ligand III or ligand III'

(III)

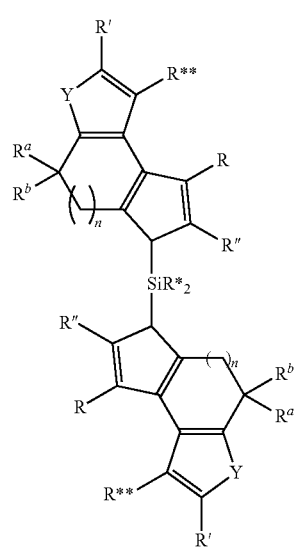
(III')

wherein R, R', R", R$^a$ and R$^b$ are each independently selected from hydrogen, or hydrocarbyl having up to 10 carbon atoms, wherein R* and R** are each independently selected from unsubstituted or substituted alkyl or aryl having up to 8 carbon atoms, including polynuclear fused aromatic rings, wherein Y is a Group 13, 14, 15 or 16 of the Periodic Table, wherein X is halogen or alkyl having up to 6 carbon atoms, and wherein n is 0, 1 or 2.

Preferably, step c) is not omitted and the silyl bridge is present.

Preferably R$^a$ and R$^b$ are the same and are hydrogen.

Preferably, n is equal to 0.

Preferably, at least one of R, R* or R** is at least as bulky as $^t$Bu.

A second aspect of the present invention provides a hydrogenated metallocene catalyst component of formula IV or IV'

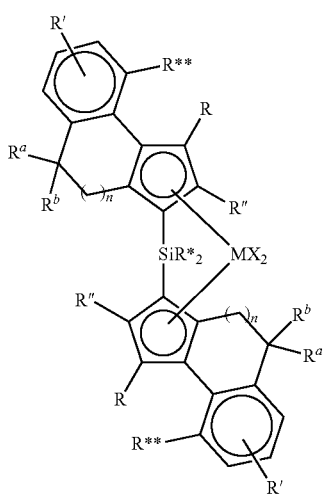
(IV)

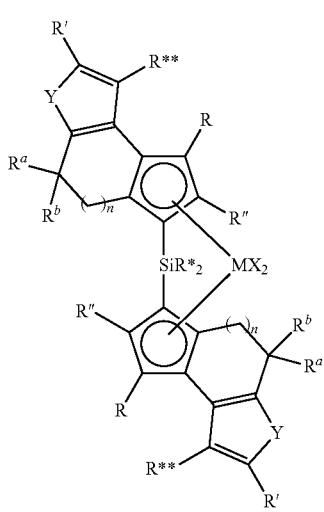

(IV')

Metallocene catalyst component of formula IV or IV' is prepared by metallation reaction of the ligand of formula III or III' by a metallic salt of formula $MX'_4$ wherein M is a metal group 4 of the Periodic Table and X' is halogen or alkyl having up to 6 carbon atoms.

This invention is particularly concerned with the preparation of ansa-metallocenes involving indenyls bearing bulky substituents on the cyclopentadienyl and/or on the phenyl fragments. This is believed to result in a very high stability of the racemic complexes toward epimerisation in solution.

A third aspect of the present invention provides a catalyst system comprising the catalyst component of formula IV or IV' and an aluminium- or boron-containing activating agent having an ionising action.

Suitable aluminium-containing activating agents comprise an alumoxane, an alkyl aluminium compound and/or a Lewis acid.

The alumoxanes that can be used in the present invention are well known and preferably comprise oligomeric linear and/or cyclic alkyl alumoxanes represented by the formula (A):

   (A)

for oligomeric linear alumoxanes; and formula (B)

   (B)

for oligomeric cyclic alumoxanes,
wherein n is 1-40, preferably 10-20; m is 3-40, preferably 3-20; and R is a $C_1$-$C_8$ alkyl group, preferably methyl. Generally, in the preparation of alumoxanes from, for example, aluminium trimethyl and water, a mixture of linear and cyclic compounds is obtained.

The amount of alumoxane and metallocene usefully employed in the preparation of a solid support catalyst can vary over a wide range. Generally the aluminium to transition metal mole ratio is in the range between 200:1 and 2000:1, preferably in the range 500:1 and 1000:1.

Suitable boron-containing activating agents may comprise a triphenylcarbenium boronate, such as tetrakis-pentafluorophenyl-borato-triphenylcarbenium as described in EP-A-0427696:

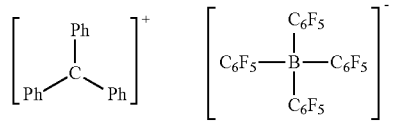

or those of the general formula below, as described in EP-A-0277004 (page 6, line 30 to page 7, line 7):

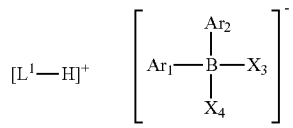

The present invention also provides a method for homo- or co-polymerising ethylene and alpha-olefins that comprises the steps of:
a) injecting into the reactor the active catalyst system of the present invention;
b) injecting into the reactor the monomer and optional comonomer;
c) maintaining under polymerisation condition;
d) retrieving a polymer.

The preferred monomers are ethylene and propylene and the preferred comonomers are propylene, 1-butene and 1-hexene.

The present invention also provides polyolefins, obtainable by the method described hereabove.

The catalyst system of the present invention may be employed in any polymerisation method such as a slurry polymerisation, a solution polymerisation, or a gas phase polymerisation, provided that the required catalytic activity is not impaired. In a preferred embodiment of the present invention, the catalyst system is employed in a solution polymerisation process, which is homogeneous, or a slurry process, which is heterogeneous. In a solution process, typical solvents include hydrocarbons having 4-7 carbon atoms such as heptane, toluene or cyclohexane. In a slurry process it is necessary to immobilise the catalyst system on an inert support.

The polyolefins prepared with the hydrogenated catalyst system of the present invention have less regio-defects and are more stereo-regular than those obtained with their non-hydrogenated counterpart.

LIST OF FIGURES

EXAMPLES

Example 1

Preparation of 2-(3,5-dimethylphenyl)-4,5-dihydro-1H-cyclopenta[a]-naphthalene and 2-(3,5-dimethylphenyl)-4,5-dihydro-3H-cyclopenta[a]-naphthalene. and of Dichloro[3,3'-bis(dimethylsilanediyl)di($\eta^5$-[2-(3,5-dimethylphenyl)-4,5-dihydro-3H-cyclopenta[a]naphthalen-3-yl)]]zirconium.

The preparation is represented by the following scheme:

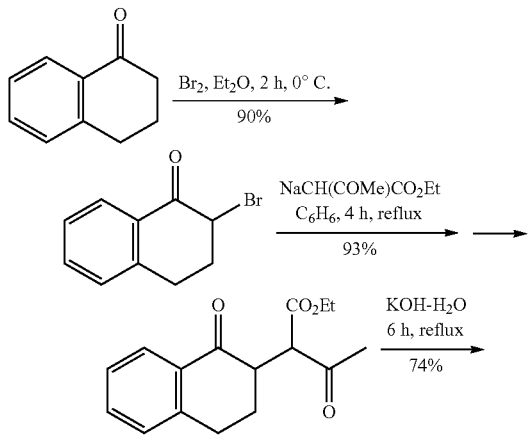

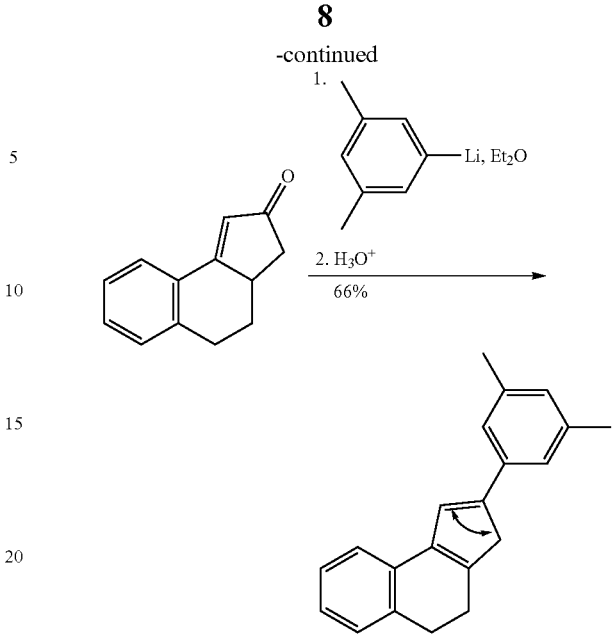

α-tetralone was brominated in the presence of diethylether ($Et_2O$) at a temperature of 0° C. for a period of time of 2 hours. It was followed by treatment with sodium salt of ethyl acetoacetate at reflux and for a period of time of 4 hours and then by cyclisation of ethyl 3-oxo-2-(1-oxo-1,2,3,4-tetrahydronaphthalen-2-yl)butanoate in the presence of base $KOH-H_2O$ at reflux and for a period of time of 6 hours to give the desired cyclopentenone with a yield of 62%. The cyclopentenone was treated with MeLi and the formed alcohol was dehydrated in order to form 2-methyl-4,5-dihydro-3aH-cyclopenta[a]naphthalene with a yield of 43%. 3,3a,4,5-Tetrahydro-2H-cyclopenta[a]-naphthalen-2-one was then reacted with 3,5-dimethylphenyllithium in ether. The acidification of the reaction mixture gave a mixture of ligands 2-(3,5-dimethylphenyl)-4,5-dihydro-3H-cyclopenta[a]-naphthalene and 2-(3,5-dimethylphenyl)-4,5-dihydro-1H-cyclopenta[a]naphthalene with a yield of 66%.

Figure 1:
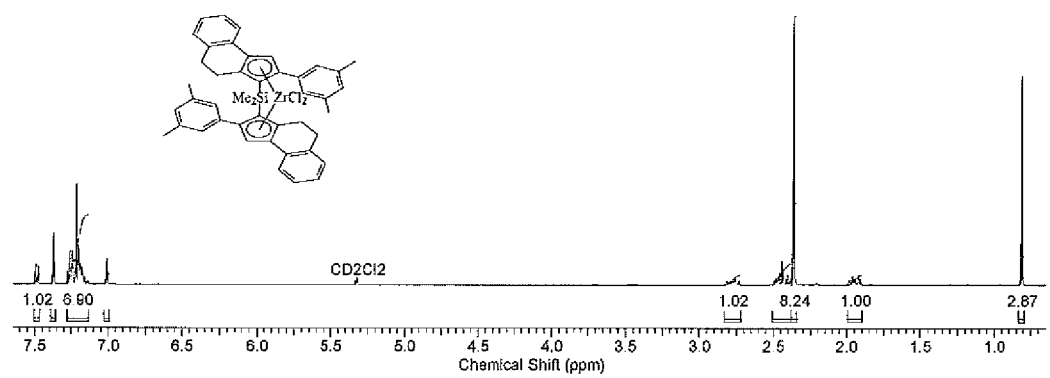
FIG. 1 represents the $^1$H NMR spectrum in $CD_2Cl_2$ of dichloro[3,3'-bis(dimethylsilanediyl)di($\eta^5$-[2-(3,5-dimethylphenyl)-4,5-dihydro-3H-cyclopenta[a]naphthalen-3-yl]]zirconium.

A lithium salt of this ligand was treated with 0.5 eqv of dichlorodimethylsilane in tetrahydrofuran (THF) to form the respective bis(cyclopentadienyl)dimethylsilane. This bis-cyclopentadienyl ligand was isolated from the crude product in low yield by a flash chromatography on Silica Gel 60. These low yield of formation of the ligands was the major difficulty encountered in synthesising the ansa-metallocenes. The chelating ligand was metallated with 2 eqv of "BuLi in toluene-hexanes and metallic salt $ZrCl_4(THF)_2$ to synthesize the desired ansa-zirconocene. This mixture was stirred overnight at room temperature and then filtered through glass frit. Crystals precipitated from the filtrate at a temperature of −30° C. were collected and dried in vacuum. NMR spectroscopy of the crystalline precipitate revealed pure racemic ansa-metallocene. $^1$H NMR spectrum of this compound (in $CD_2Cl_2$) is shown in the FIG. 1. This rac-complex was isolated with a yield of 52% resulting from the high stability of this isomer as compared with its meso-counterpart.

US 8,426,613 B2

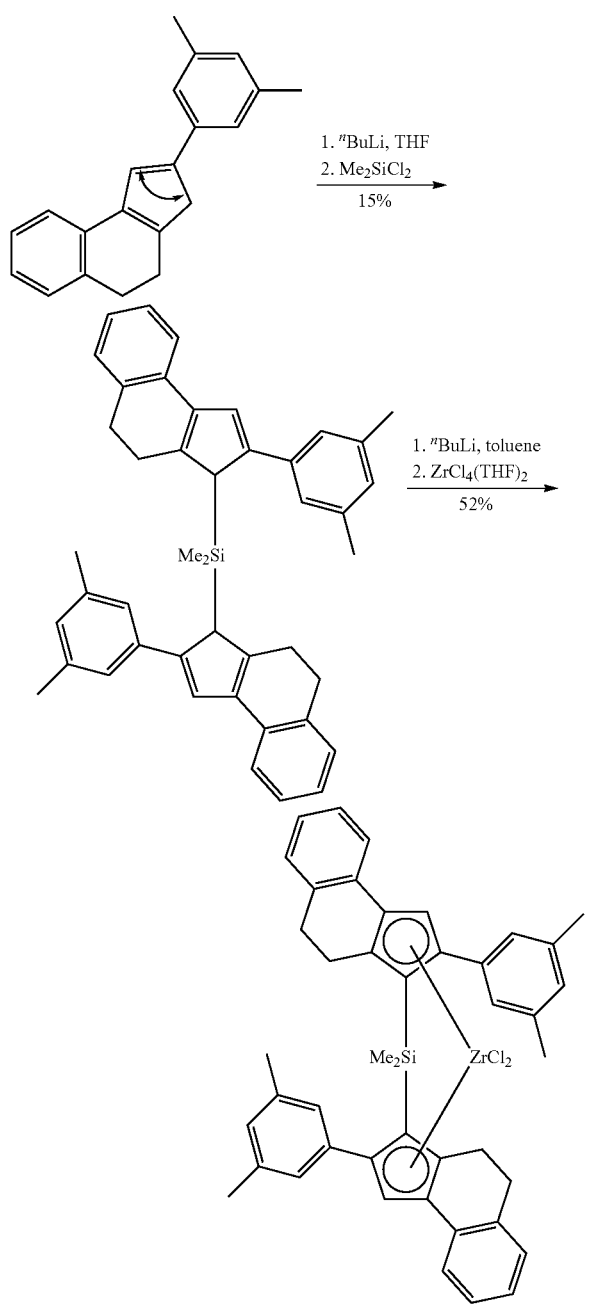

Figure 2:
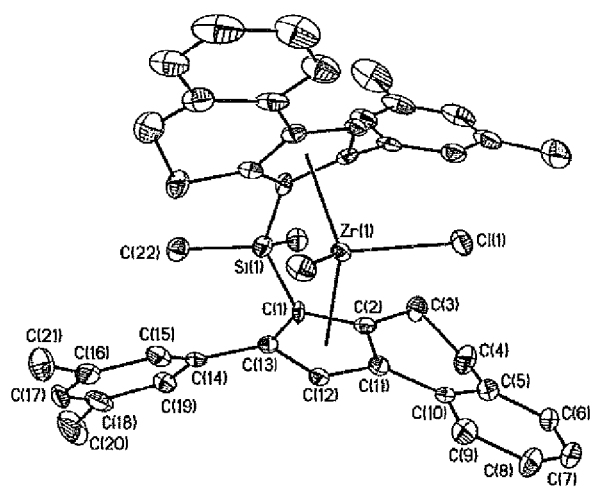
FIG. 2 is the ORTEP representation of the molecular structure of dichloro[3,3'-bis(dimethylsilanediyl)di($\eta^5$-[2-(3,5-dimethylphenyl)-4,5-dihydro-3H-cyclopenta[a]naphthalen-3-yl]]zirconium wherein thermal ellipsoids are drawn at the 50% probability level.

This ansa-zirconocene was successfully characterised by X-ray crystal structure analysis. FIG. 2 is the ORTEP representation of the molecular structure of this complex involving 2-(3,5-dimethylphenyl)-4,5-dihydrocyclopenta[a]naphthyl fragment wherein thermal ellipsoids are drawn at the 50% probability level.

The key geometric parameters of the first independent molecule are as follows:

bond length Zr-Cp(c)=2.234(1) Angströms;

angle between two cyclopentadienyl planes=61.0°.

The key geometric parameters of the second independent molecule are as follows:

bond length Zr-Cp(c)=2.238(1) Angströms;

angle between two cyclopentadienyl planes=59.6°.

Both independent molecules represent the respective racemic complexes.

Example 2

Preparation of 2-(4-tert-butylphenyl)-4,5-dihydro-1H-cyclopenta[a]naphthalene and 2-(4-tert-butylphenyl)-4,5-dihydro-3H-cyclopenta[a]naphthalene. and of Dichloro[3,3'-bis(dimethylsilanediyl)di($\eta^5$-[2-(4-tert-butylphenyl)-4,5-dihydro-3H-cyclopenta[a] naphthalen-3-yl]]zirconium The preparation proceeds as in example 1 except that in the final step for preparing the ligand one equivalent of 4-tert-butylphenyllithium in ether is added to 3,3a,4,5-tetrahydro-2H-cyclopenta[a]naphthalen-2-one, followed by acidification of the reaction mixture. The final ligand is a mixture of 2-(4-tert-butylphenyl)-4,5-dihydro-3H-cyclopenta[a]naphthalene and 2-(4-tert-butylphenyl)-4,5-dihydro-1H-cyclopenta[a]naphthalene obtained with a yield of 76%, as represented in the scheme herebelow.

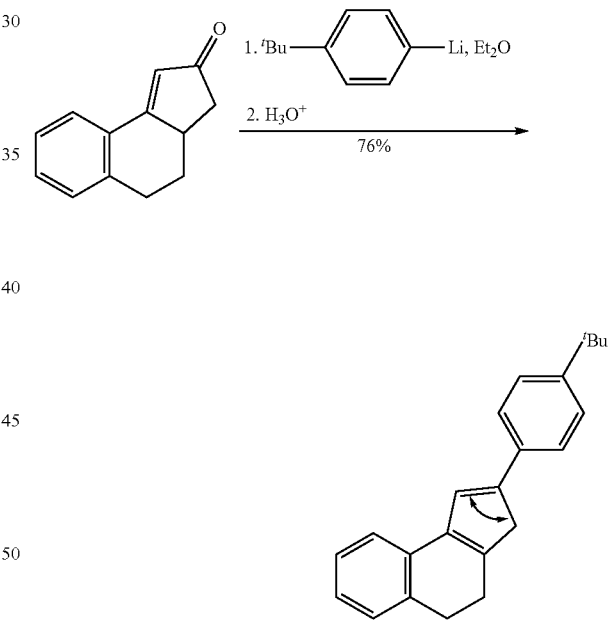

Figure 3:
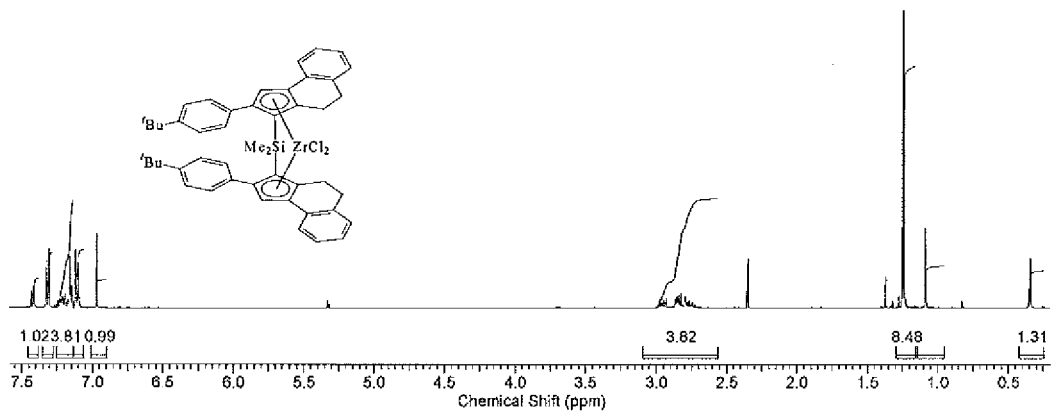
FIG. 3 represents the $^1$H NMR spectrum of dichloro[3,3'-bis(dimethylsilanediyl) di($\eta^5$-[2-(4-tert-butylphenyl)-4,5-dihydro-3H-cyclopenta[a]naphthalen-3-yl]]zirconium in $CD_2Cl_2$.

Lithium salts of these ligands were treated with 0.5 eqv of dichlorodimethylsilane in THF to form the respective bis(cyclopentadienyl)dimethylsilanes. This mixture of bis-cyclopentadienyl ligands was isolated from the crude product in low yield by a flash chromatography on Silica Gel 60. Next, this chelating ligand was metallated with 2 equivalents of "BuLi in toluene-hexanes, and metallic salt ZrCl$_4$(THF)$_2$. This mixture was stirred overnight at room temperature and then filtered through glass frit. Crystals precipitated from the filtrate at −30° C. were collected and dried in vacuum. On the evidence of NMR spectroscopy, this crystalline precipitate is pure meso ansa-metallocene. $^1$H NMR spectrum of this compound (in $CD_2Cl_2$) is shown in FIG. 3. This meso-complex was isolated with a yield of 16%.

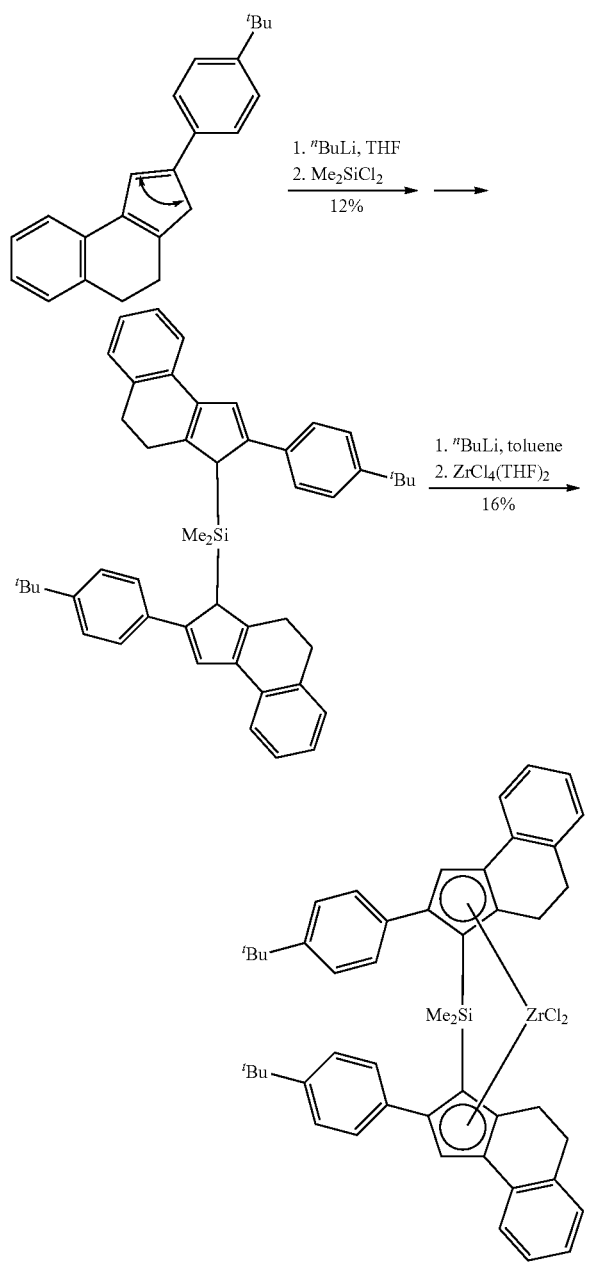

Figure 4:
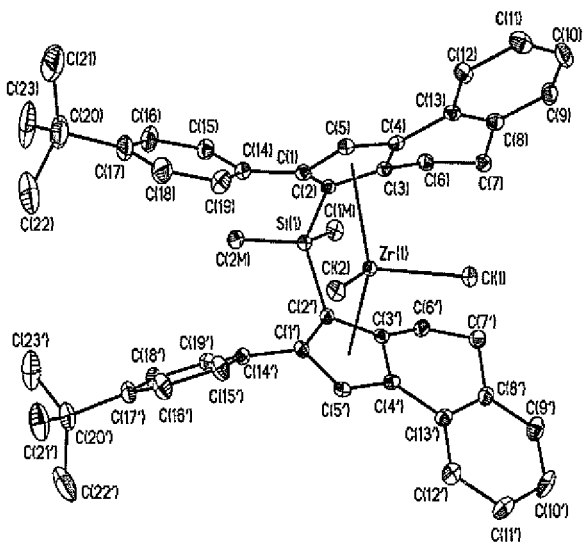
FIG. 4 is the ORTEP representation of the molecular structure of dichloro[3,3'-bis(dimethylsilanediyl)di($\eta^5$-[2-(4-tert-butylphenyl)-4,5-dihydro-3H-cyclopenta[a]naphthalen-3-yl]]zirconium wherein thermal ellipsoids are drawn at the 50% probability level.

The meso-complex was characterised by X-ray crystal structure analysis. The ORTEP representation of its molecular structure can be seen in FIG. 4. The key geometric parameters of this structure are the following:

bond lengths Zr-Cp(c) and Zr-Cp(c)' are respectively 2.234 (1) and 2.237(1) Angströms;
bond angle Cp(c)-Zr-Cp(c)' is 127.6°.

Example 3

Preparation of 2-phenyl-8-tert-butyl-4,5-dihydro-1H-cyclopenta[a]naphthalene and 2-phenyl-8-tert-butyl-4,5-dihydro-3H-cyclopenta[a]naphthalene. and of Dichloro[3,3'-bis(dimethylsilanediyl)di($\eta^5$-(8-tert-butyl-2-phenyl-4,5-dihydro-3H-cyclopenta[a]naphthalen-3-yl)]zirconium The preparation is described in the following scheme.

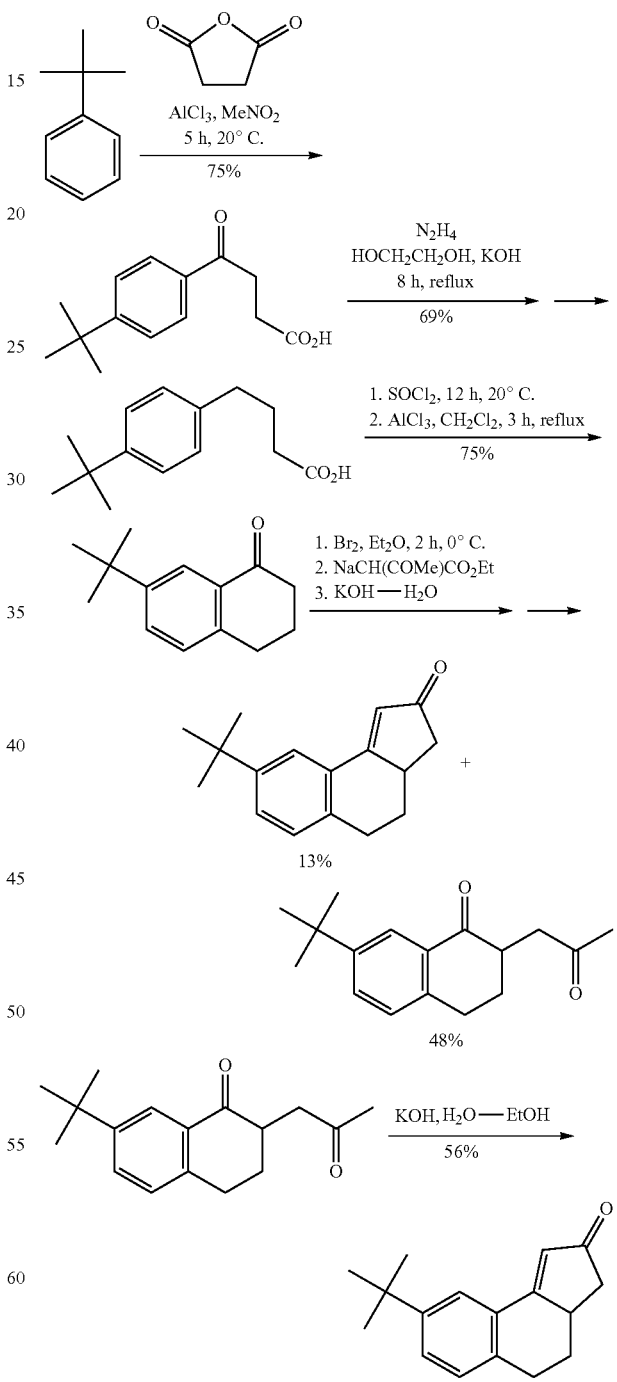

Starting material tert-butyl benzene was acylated to form a keto-acid that was subsequently reduced. Cyclisation of the resulting product was then carried out in the presence of AlCl₃ to give 7-tert-butyl-3,4-dihydronaphthalen-1(2H-1)-one and with an overall yield of 39%. Bromination of this product, followed by alkylation and cyclisation in aqueous KOH gave a mixture of 8-tert-butyl-3,3a,4,5-tetrahydro-2H-1-cyclopenta[a]naphthalen-2-one and 7-tert-butyl-2-(2-oxopropyl)-3,4-dihydronaphthalen-1(2H)-one in a 1/3.5 ratio. The undesired 7-tert-butyl-2-(2-oxopropyl)-3,4-dihydronaphthalen-1(2H)-one was isolated and treated in alcoholic KOH to give the desired 8-tert-butyl-3,3a,4,5-tetrahydro-2H-cyclopenta[a]naphthalen-2-one in moderate yield. The latter product was further reacted with one equivalent of PhLi in ether followed by acidification of the reaction medium to give a mixture of 2-phenyl-8-tert-butyl-4,5-dihydro-1H-cyclopenta[a]naphthalene and 2-phenyl-8-tert-butyl-4,5-dihydro-3H-cyclopenta[a]naphthalene as shown in the scheme below

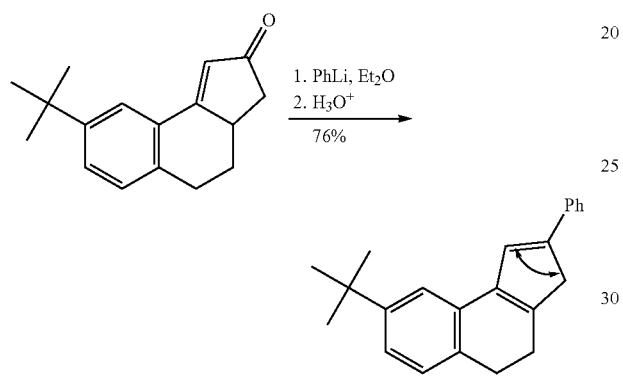

Figure 5:
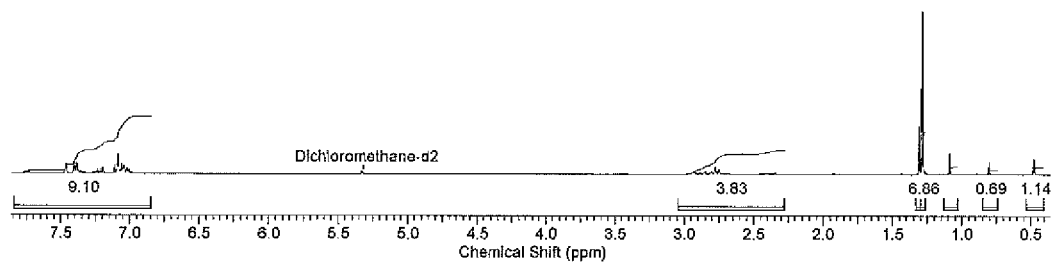
FIG. 5 represents the $^1$H NMR spectrum in $CD_2Cl_2$ of dichloro[3,3'-bis(dimethylsilanediyl)di($\eta^5$-(8-tert-butyl-2-phenyl-4,5-dihydro-3H-cyclopenta[a]naphthalen-3-yl)]zirconium.
Figure 6:
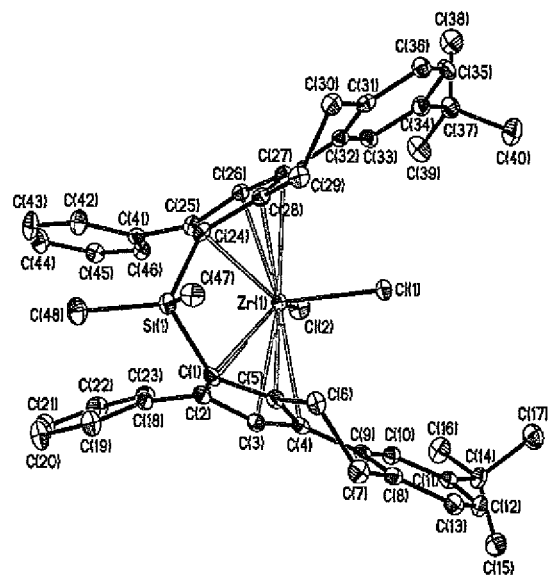
FIG. 6 is the ORTEP representation of the molecular structure of dichloro[3,3'-bis(dimethylsilanediyl)di($\eta^5$-(8-tert-butyl-2-phenyl-4,5-dihydro-3H-cyclopenta[a]naphthalen-3-yl)]zirconium.

The lithium salt of this ligand was treated with 0.5 eqv of Me₂SiCl₂ in THF to form the respective bis(cyclopentadienyl)dimethylsilane. This bis-cyclopentadienyl ligand was isolated from the crude product with a yield of 18% repeating flash chromatography on Silica Gel 60. It was metallated with 2 eqv of ⁿBuLi in toluene-hexanes, and then with metallic salt ZrCl₄(THF)₂. This mixture was stirred overnight at room temperature and then filtered through glass frit. Crystals precipitated from the filtrate at a temperature of −30° C. were collected and dried in vacuum. On the evidence of ¹H NMR spectroscopy, this product isolated with a yield of 21% is a mixture of rac- and meso-complexes in a ratio of 1 to 4. This ¹H NMR spectrum is shown in FIG. 5. The meso-isomer was characterised by X-ray crystal structure analysis. FIG. 6 is the ORTEP representation of the molecular structure of this meso-complex with thermal ellipsoids drawn at the 50% probability level.

The key geometric parameters of this structure are:
bond lengths Zr-Cp(c) and Zr-Cp(c)' are respectively 2.222 (1) and 2.221(1) Angströms;
angle between two cyclopentadienyl planes is 56.4°.

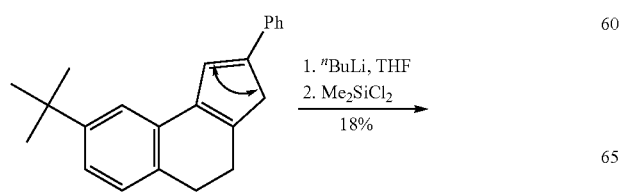

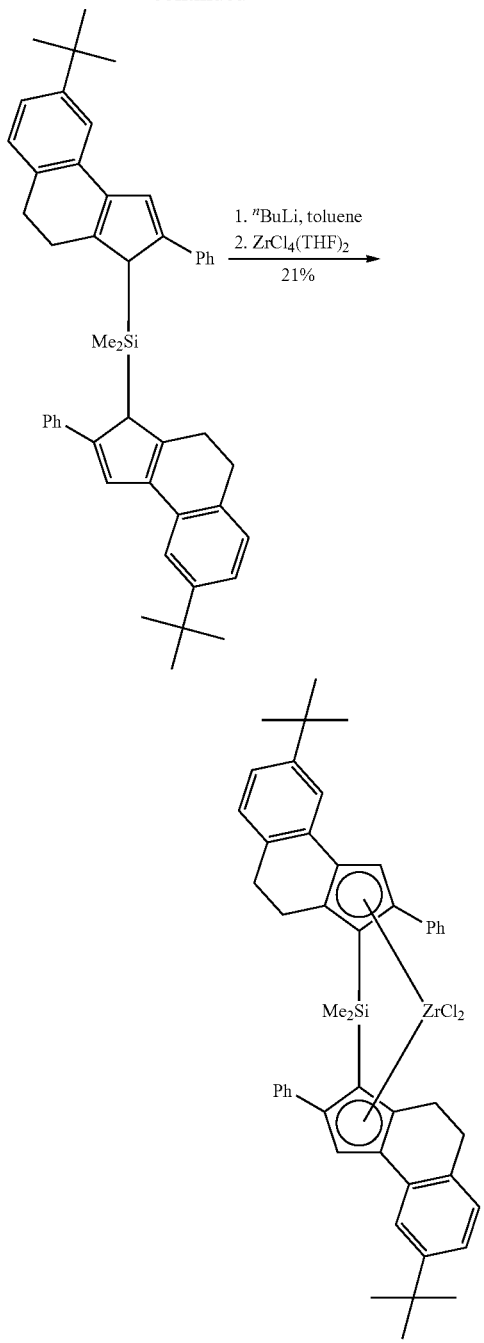

Example 4

Preparation of 3,3a,4,5-tetrahydro-2H-cyclopenta[c]-phenanthren-2-one and of Bis[η⁵-(2-phenyl-4,5-dihydro-3H-cyclopenta[c]phenanthren-3-yl)zirconium dichloride.

This complex was prepared starting from naphthalene and following a scheme similar to that of example 3 as seen herebelow.

15

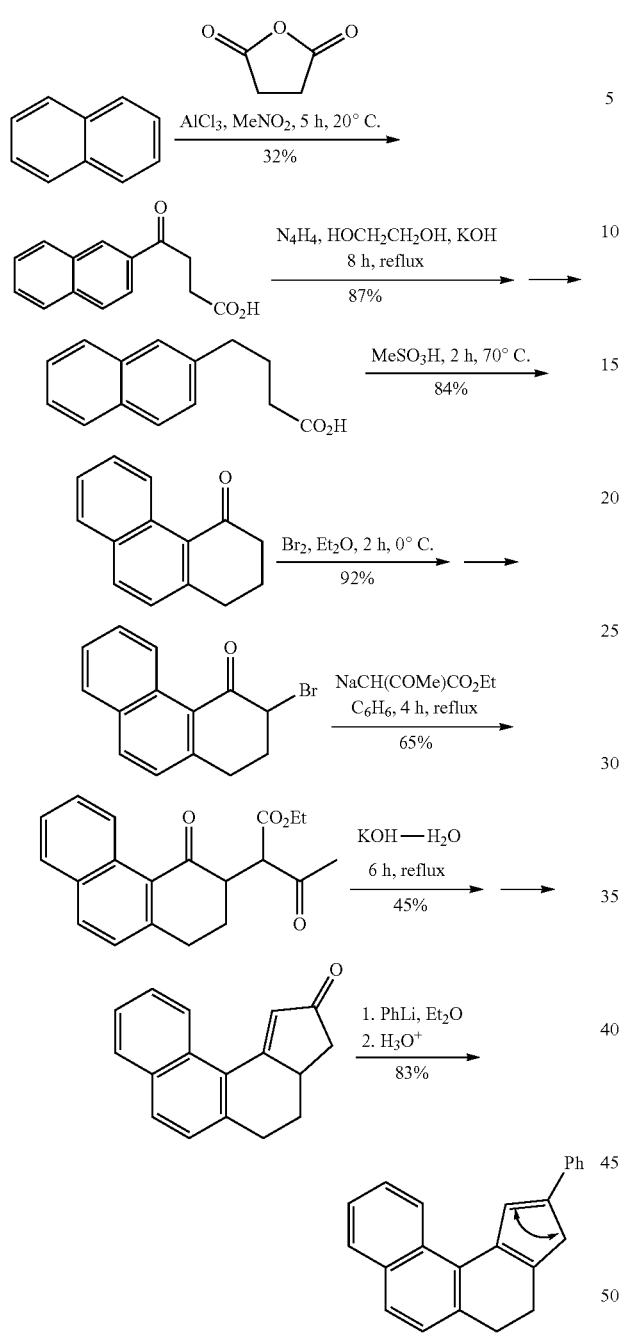

The chelating ligand was metallated with 2 equivalents of "BuLi in toluene-hexanes followed by addition of metallic salt ZrCl$_4$(THF)$_2$ to form the unbridged metallic complex.

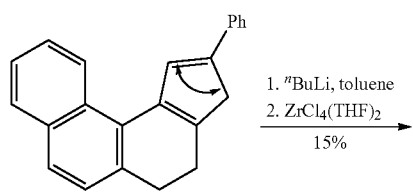

16
-continued

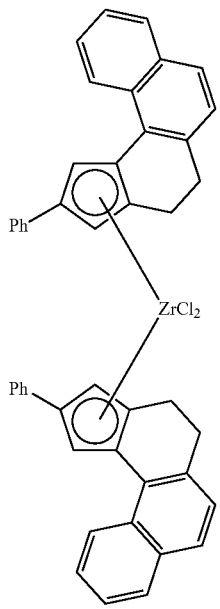

Figure 7:
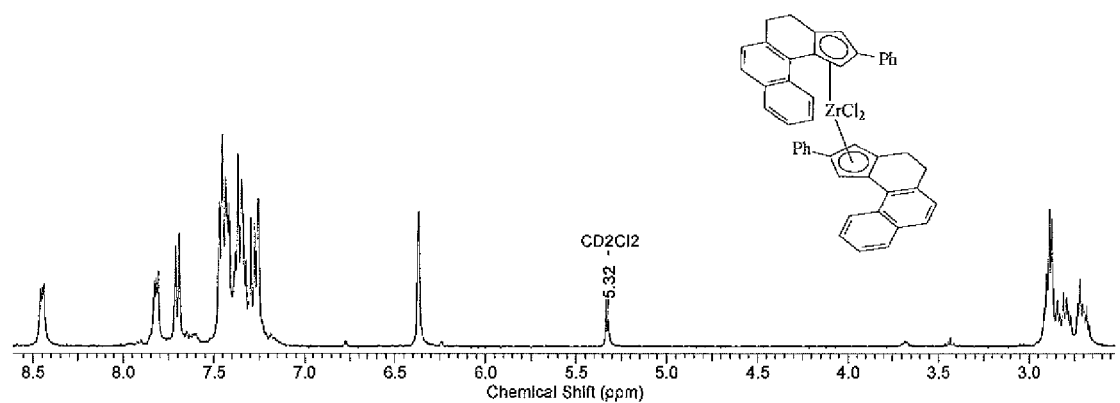
FIG. 7 represents the $^1$H NMR spectrum in $CD_2Cl_2$ of bis[$\eta^5$-(2-phenyl-4,5-dihydro-3H-cyclopenta[c]phenanthren-3-yl)zirconium dichloride.

The rac-complex was unambiguously characterised by NMR spectroscopy as seen in FIG. 7 and by X-ray crystal structure analysis.

Figure 8:
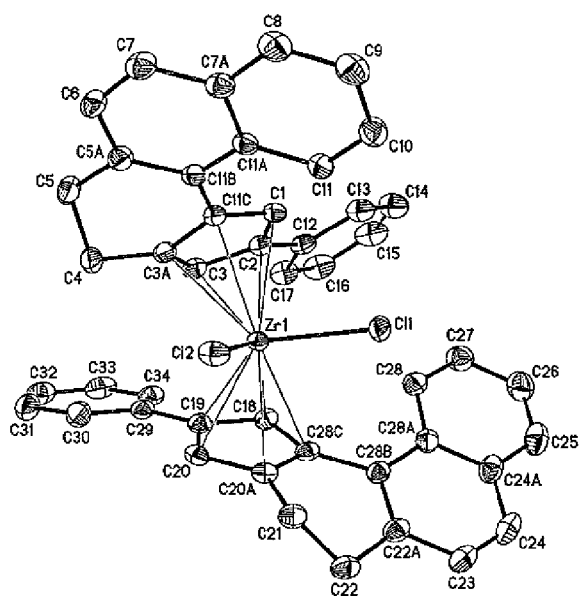
FIG. 8 is the ORTEP representation of the molecular structure of bis[$\eta^5$-(2-phenyl-4,5-dihydro-3H-cyclopenta[c]phenanthren-3-yl)zirconium dichloride.

FIG. 8 is the ORTEP representation of the molecular structure of the racemic complex with thermal ellipsoids drawn at the 50% probability level. The key geometric parameters of this structure are:
bond lengths of Zr-Cp(c) and Zr-Cp(c)' are respectively 2.229(2) and 2.244(2) Angströms;
angle between Zr-Cp(A) and Zr-Cp'(A) axis is 132.70(6)°, angle between Cp and Cp' planes is 50.91(6)°.

It was observed that rotation in this unbridged metallic complex was hindered by the presence of the very bulky substituents.

Example 5

Preparation of dichloro[6,6'-bis(dimethylsilanediyl) di($\eta^5$-(7-phenyl-5,6-dihydro-4H-indeno[5,4-b] thiophene-6-yl)]zirconium The preparation is described in the following scheme.

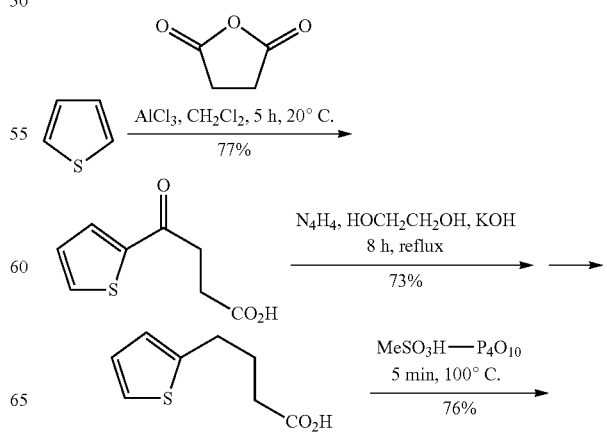

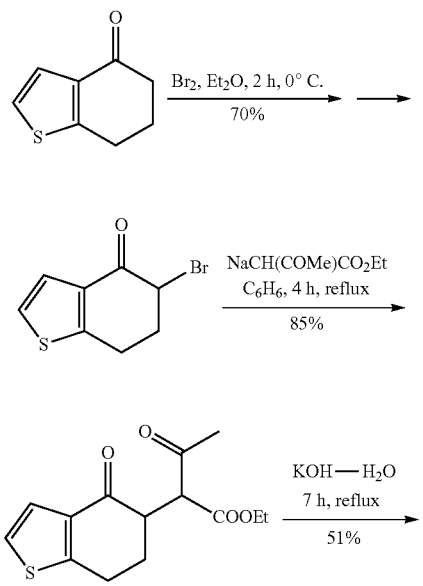

6,7-dihydro-1-benzothiophen-4(5H)-one was obtained with an overall yield of 43% via the acylation of thiophene by succinic anhydride followed by reduction of the ketone formed and by the cyclisation of 4-(2-thienyl)butanoic acid in the presence of the laton's reagent. Next, 4,5,5a,6-tetrahydro-7H-indeno[5,4-b]thiophen-7-one was synthesised from 6,7-dihydro-1-benzothiophen-4(5H)-one with an overall yield of 30%. The latter product was further reacted with one equivalent of PhLi in ether followed by acidification of the reaction medium to give a mixture of 7-phenyl-5,5a-dihydro-4H-indeno[5,4-b]thiophene and 7-phenyl-5,8-dihydro-4H-indeno[5,4-b]thiophene as shown in the scheme below

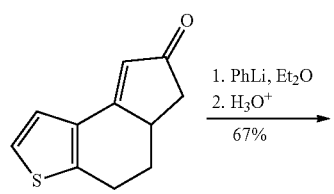

Figure 9:
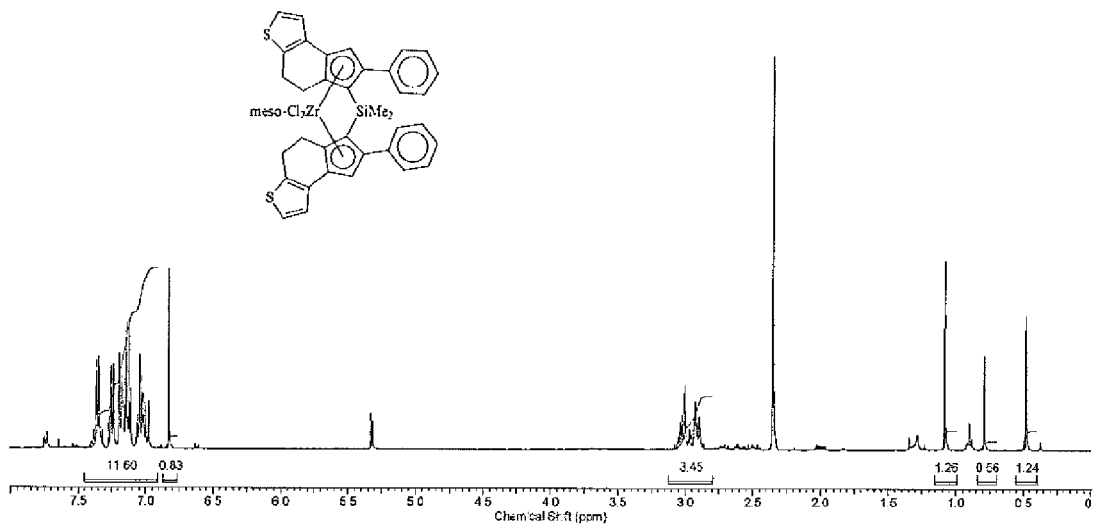
FIG. 9 represents the $^1$H NMR spectrum in $CD_2Cl_2$ of dichloro[6,6'-bis(dimethylsilanediyl)di($\eta^5$-(7-phenyl-5,6-dihydro-4H-indeno[5,4-b]thiophene-6-yl)]zirconium.
Figure 10:
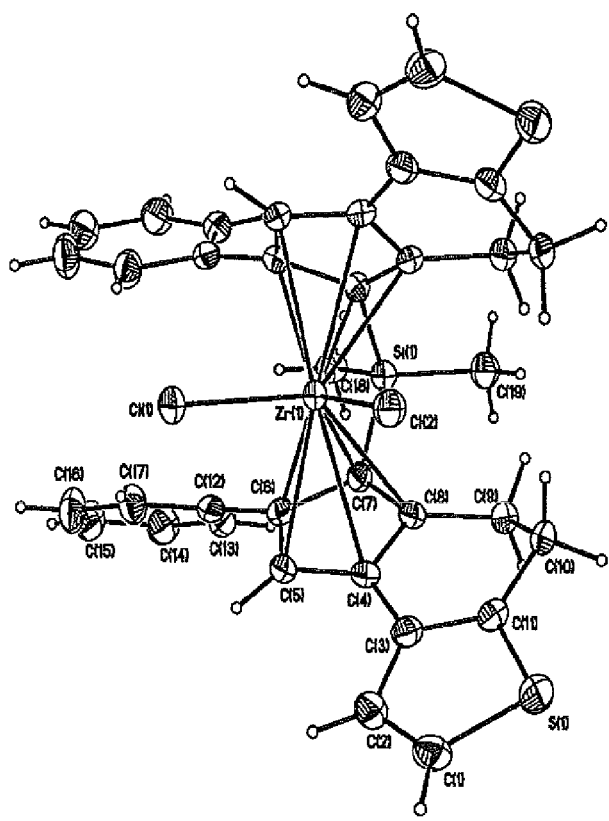
FIG. 10 is the ORTEP representation of the molecular structure of dichloro[6,6'-bis(dimethylsilanediyl)di($\eta^5$-(7-phenyl-5,6-dihydro-4H-indeno[5,4-b]thiophene-6-yl)]zirconium.

The lithium salt of this ligand was treated with 0.5 eqv of Me₂SiCl₂ in THF to form the respective bis(cyclopentadienyl)dimethylsilane. This bis-cyclopentadienyl ligand was isolated as a mixture of the Me₂Si-bridging ligands involving ca. 70% of the desired isomers with a yield of 17% by repeating flash chromatography on Silica Gel 60. It was metallated with 2 eqv of "BuLi in toluene-hexanes, and then with metallic salt ZrCl₄(THF)₂. This mixture was stirred overnight at room temperature and then filtered through glass frit. Crystals precipitated from the filtrate at a temperature of −30° C. were collected and dried in vacuum. On the evidence of ¹H NMR spectroscopy, this product isolated with a yield of 13% is a mixture of rac- and meso-complexes in a ratio of 1 to 5. This ¹H NMR spectrum is shown in FIG. 9. The meso-isomer was characterised by X-ray crystal structure analysis. FIG. 10 is the ORTEP representation of the molecular structure of this meso-complex with thermal ellipsoids drawn at the 50% probability level.

The key geometric parameters of this structure are:
bond lengths Zr-Cp(c) and Zr-Cp(c)' are 2.239(1) Angstroms;
angle between two cyclopentadienyl planes is 59.2°.

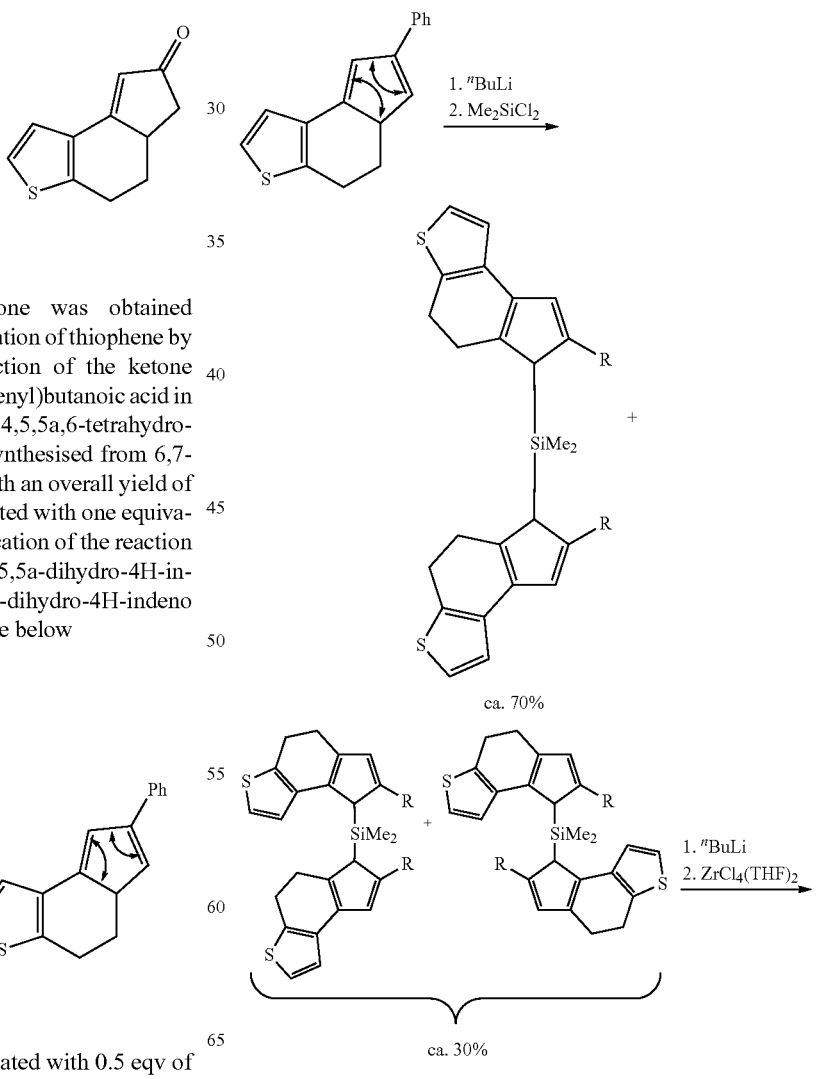

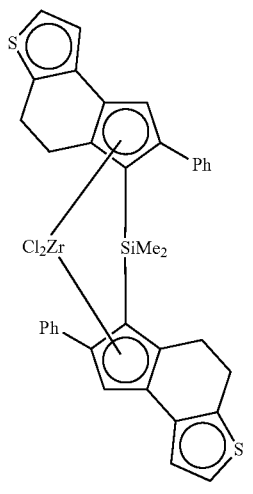

The invention claimed is:

1. A method for preparing substituted bis-tetrahydroindenyl ligands that comprises a) preparing a complex of general formula I or I'

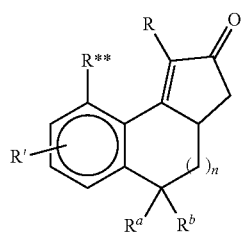
(I)

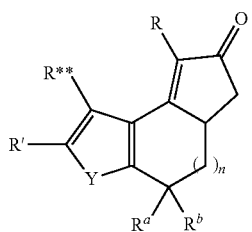
(I')

b) reacting complex I or complex I' with R"Li followed by acidification with a diluted acid in order to prepare complex II or complex II'

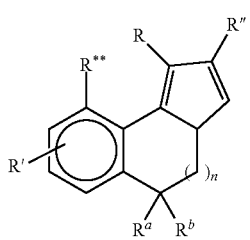
(II)

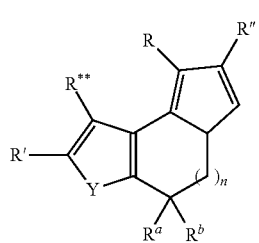
(II')

c) optionally reacting complex II or complex II' with $R^*_2SiX_2$ in the presence of nBuLi in order to prepare ligand III or ligand III'

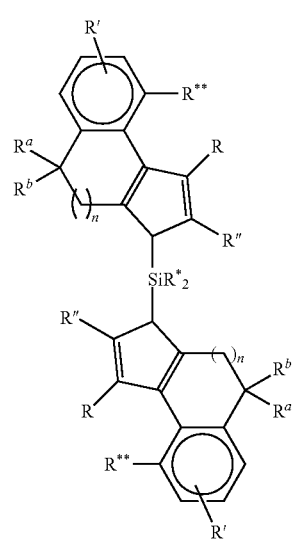
(III)

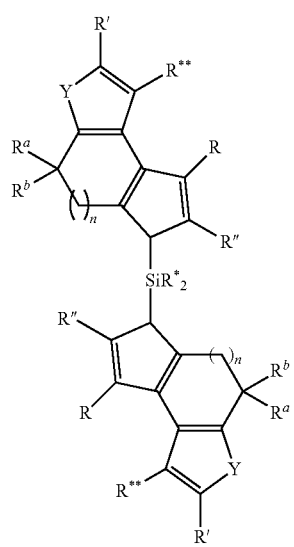
(III')

wherein R, R', R", $R^a$ and $R^b$ are each independently selected from hydrogen, or hydrocarbyl having up to 10 carbon atoms, wherein R* and R** are each independently selected from unsubstituted or substituted alkyl or aryl having up to 8 carbon atoms, including polynuclear fused aromatic rings, wherein Y is a Group 13, 14, 15 or 16 of the Periodic Table,
wherein X is halogen or alkyl having up to 6 carbon atoms, and
wherein n is 0, 1 or 2.

2. The method of claim 1 wherein step c) is present.

3. The method of claim 1 wherein $R^a$ and $R^b$ are the same and are hydrogen.

4. The method of claim 1 wherein at least one of R, R* or R** is at least as bulky as tert-butyl.

5. The method of claim 1 wherein n is zero.

6. Ligand of formula III or formula III' obtained by the method of claim 1.

* * * * *